United States Patent [19]

Baron

[11] Patent Number: 4,708,140

[45] Date of Patent: Nov. 24, 1987

[54] ATRAUMATIC VASCULAR BALLOON CLAMP

[76] Inventor: Howard C. Baron, 222 E. Nineteenth St., New York, N.Y. 10003

[21] Appl. No.: 860,995

[22] Filed: May 8, 1986

[51] Int. Cl.$^4$ ............................................. A61B 17/12
[52] U.S. Cl. .................................. 128/325; 128/346; 128/327
[58] Field of Search .............................. 128/325–327, 128/344, DIG. 25, 346, 686

[56] References Cited

U.S. PATENT DOCUMENTS

| | | |
|---|---|---|
| 2,756,753 | 7/1956 | Means . |
| 2,921,584 | 1/1960 | Di Vette . |
| 3,126,005 | 3/1964 | Smialowski . |
| 3,270,745 | 9/1966 | Wood . |
| 3,332,654 | 7/1967 | Jacobson . |
| 3,361,133 | 1/1968 | Kimberley et al. . |
| 3,507,270 | 4/1970 | Ferrier . |
| 3,516,408 | 6/1970 | Montanti . |
| 3,538,917 | 11/1970 | Selker . |
| 3,675,656 | 7/1972 | Hakim . |
| 3,730,186 | 5/1973 | Edmunds, Jr. . |
| 3,744,063 | 7/1973 | McWhorter . |
| 3,831,583 | 8/1974 | Edmunds, Jr. . |
| 3,834,394 | 2/1974 | Hunter et al. . |
| 3,854,469 | 12/1974 | Giori et al. . |
| 3,863,622 | 2/1975 | Buuck . |
| 3,889,685 | 6/1975 | Miller et al. . |
| 3,903,894 | 9/1975 | Rosen et al. . |
| 3,952,747 | 4/1976 | Kimmell, Jr. . |
| 4,118,805 | 10/1978 | Reimels . |
| 4,140,125 | 2/1979 | Smith . |
| 4,178,915 | 12/1979 | Szinicz et al. . |
| 4,222,377 | 9/1980 | Burton . |
| 4,256,094 | 3/1981 | Kapp et al. . |
| 4,399,809 | 8/1983 | Baro et al. . |
| 4,404,971 | 9/1983 | Le Veen et al. ................ 128/325 X |
| 4,408,597 | 10/1983 | Tenney, Jr. . |
| 4,419,095 | 12/1983 | Nebergall et al. . |
| 4,428,365 | 1/1984 | Hakky ..................... 128/DIG. 25 X |
| 4,478,219 | 10/1984 | Rozario et al. ...................... 128/325 |
| 4,531,519 | 7/1985 | Dunn et al. ........................ 128/327 |
| 4,586,501 | 5/1986 | Claracq ........................... 128/326 X |

OTHER PUBLICATIONS

Khouri et al., "An Inflatable Cuff for Zero Determination in Blood Flow Studies", Journal of Applied Physiology, vol. 23, pp. 395–397 (1967).
In Vivo Metric Systems, "Instructions for Blood Vessel Occluders Model VO-3, VO-4 and VO-4B", (1966).
Netherlands Patent Application No. 8105304 (Nov. 24, 1981).
Dunn, "The Use of the Arterial Sling Tourniquet in Surgical Practice", Brit. J. Surg., 1973, vol. 60, No. 8, pp. 594–596, Aug.

Primary Examiner—Michael H. Thaler
Attorney, Agent, or Firm—Banner, Birch, McKie & Beckett

[57] ABSTRACT

A clamp, and method, for occluding bodily vessels such as arteries and veins, is provided. The clamp comprises a flexible hollow catheter having a pair of inflatable balloons sealed to the catheter and in fluid communication with its interior. The balloons are separated by a predetermined distance along the catheter such that when the catheter is secured around a vessel, the balloons present substantially parallel, opposed and spaced occluding surfaces at substantially opposite sides of the vessel. Lateral expansion spaces also are formed into which the compressed vessel wall expands as the vessel is compressed when the balloons are inflated by a fluid introduced through the catheter.

13 Claims, 4 Drawing Figures

ATRAUMATIC VASCULAR BALLOON CLAMP

BACKGROUND OF THE INVENTION

The present invention relates to clamps for preventing the flow of fluids through bodily vessels and, more particularly, to an atraumatic clamp for occluding blood vessels during surgery.

Typical prior art vessel occluding devices are designed in "O", "J" or "C" shapes with vessel contacting surfaces on their inner aspects which completely surround the vessel. When occluding pressure is applied to the vessel (such as by inflation of one or more balloons within the device in contact with the vessel), the vessel is compressed by a constricting force applied around its entire circumference. Some examples of these types of prior art devices are described below.

It has been observed that significant trauma to the vessel often results from the use of such prior art occluding devices. Applicant has discovered that the cause of this trauma is attributed to the design of these devices and the way in which they apply compressive forces to the vessel. Specifically, the radially directed compressive forces applied completely around the circumference of the vessel preclude lateral extension of the vessel, thus forcing the vessel tissue to compress longitudinally—a direction in which it has relatively little compliance. The high compressive forces required to effect this longitudinal compression and occlusion of the lumen of the vessel result in an actual crushing of the vessel tissue, with consequent damage. The trauma is aggravated in the case of diseased vessels, such as those suffering from the effects of arteriosclerosis. The thickened and hardened vessel wall exhibits less than the normal degree of compliance upon compression, and the encircling compressive forces of the prior art clamps do not accommodate localized excessive thickening.

U.S. Pat. No. 4,399,809 to Baro et al. discloses an artificial sphincter designed to be wrapped around an intestine or other anatomical vessel. One embodiment of the artificial sphincter comprises a flexible strip having attached thereto a plurality of inflatable chambers interconnected by tubing. A gas supply tube is also provided to one of the chambers. When the strip is wrapped around the vessel, the strip and inflatable chambers form a circular (i.e., O-shaped) clamp having four simultaneously inflatable chambers, each of the chambers exerting pressure when inflated on one quadrant of the vessel. Unfortunately, this circular type of clamp, which applies pressure to the entire circumference of the vessel, is unable to provide sufficient compressive force to occlude the vessel's inner lumen without damaging the vessel.

Similarly, "C" and "J" balloon clamps having one or more inflatable balloons along the inner aspect of the curved portions of C-shaped or J-shaped frames suffer from the same disadvantages, namely, an undesirable degree of trauma imparted to the vessel in order to achieve complete occlusion of the inner lumen.

U.S. Pat. No. 4,222,377 to Burton discloses a circular artificial sphincter having three inflatable balloons positioned along and completely covering the inner aspect of an O-shaped frame. Although the Burton device is specifically designed as an artificial sphincter for treating incontinence, because of its design it too can impart an undesirable degree of trauma to the vessels which it is designed to occlude.

U.S. Pat. No. 4,408,597 to Tenney, Jr. discloses a circular clamp for occluding the lumen of an internal organ. The clamp comprises a circular (i.e., O-shaped) frame having two inflatable balloons positioned along the inner aspect. One of the two balloons is always inflated while the second balloon may be inflated or deflated in order to control the degree of occluding presure applied to the vessel. Accordingly, the two balloons are not simultaneously inflatable. Even though only two balloons are provided, this type of clamp also can impart significant traumatic damage to the vessel due to the fact that the two balloons engage substantially the entire circumference of the O-shaped frame.

U.S. Pat. No. 4,404,971 to LeVeen et al. discloses a completely different type of device for occluding the flow of fluid through a bodily vessel. The LeVeen device comprises a hollow catheter having two inflatable balloons disposed along the length of the catheter, spaced apart from one another. The catheter and the balloons (in a deflated condition) are threaded into the interior of the vessel. Once the catheter and balloons are positioned completely within the vessel, air is pumped through the catheter in order to inflate the balloons. The balloons expand within the interior of the vessel until contact is made around the entire inner circumference of the vessel wall. Accordingly, each of the balloons acts to independently stop fluid flow through the vessel. Drawbacks to the use of this type of device include the need for a surgical incision in the vessel itself, and difficulties involved with threading and positioning the catheter and balloons in the vessel.

SUMMARY OF THE INVENTION

Accordingly, it is an object of the present invention to provide a vascular clamp which is simple in construction and easy to use.

It is another object of the present invention to provide a vascular clamp able to effectively occlude the lumen of a vessel without imparting significant trauma to the vessel.

It has been discovered that the key to atraumatic vessel occlusion is to provide properly directed compressive forces along only portions of the vessel circumference, and radial or lateral expansion space for the vessel wall as it is compressed. Compliant occluding surfaces, such as the opposed parallel surfaces of inflatable balloons, preferably are used to apply the compressive forces. These nonencircling resilient surfaces can accommondate for irregularities in vessel wall thickness, such as localized excessive thickening of the vessel wall in the case of an arteriosclerotic vessel.

The above and other objects of the invention, which will become apparent to those skilled in the art from the description of several embodiments of the invention appearing hereinafter, are met by a novel clamp and method for occluding a vessel. The clamp comprises a flexible catheter adapted to be connected to a fluid source. The catheter has a pair of spaced inflatable balloons, each of the balloons being positioned along a portion of the catheter. The balloons are in fluid communication with the interior of the catheter and are separated from one another by a predetermined distance along and sealed to the exterior of the catheter. Means is provided for securing the catheter in a closed loop around the vessel with the balloons presenting substantially parallel, opposed and spaced occluding surfaces on substantially opposite sides of the vessel with lateral expansion spaces for the vessel tissue adjacent the ends of the balloons, whereby inflation of the balloons clamps the vessel therebetween to close the lumen. The vessel wall expands laterally into the expansion spaces as it is compressed. The novel method involves the use of this inventive clamp.

The term "vessel" as used herein includes natural bodily vessels, such as arteries and veins, as well as surgically implanted synthetic vessels, such as synthetic bypass grafts.

Figure 1:
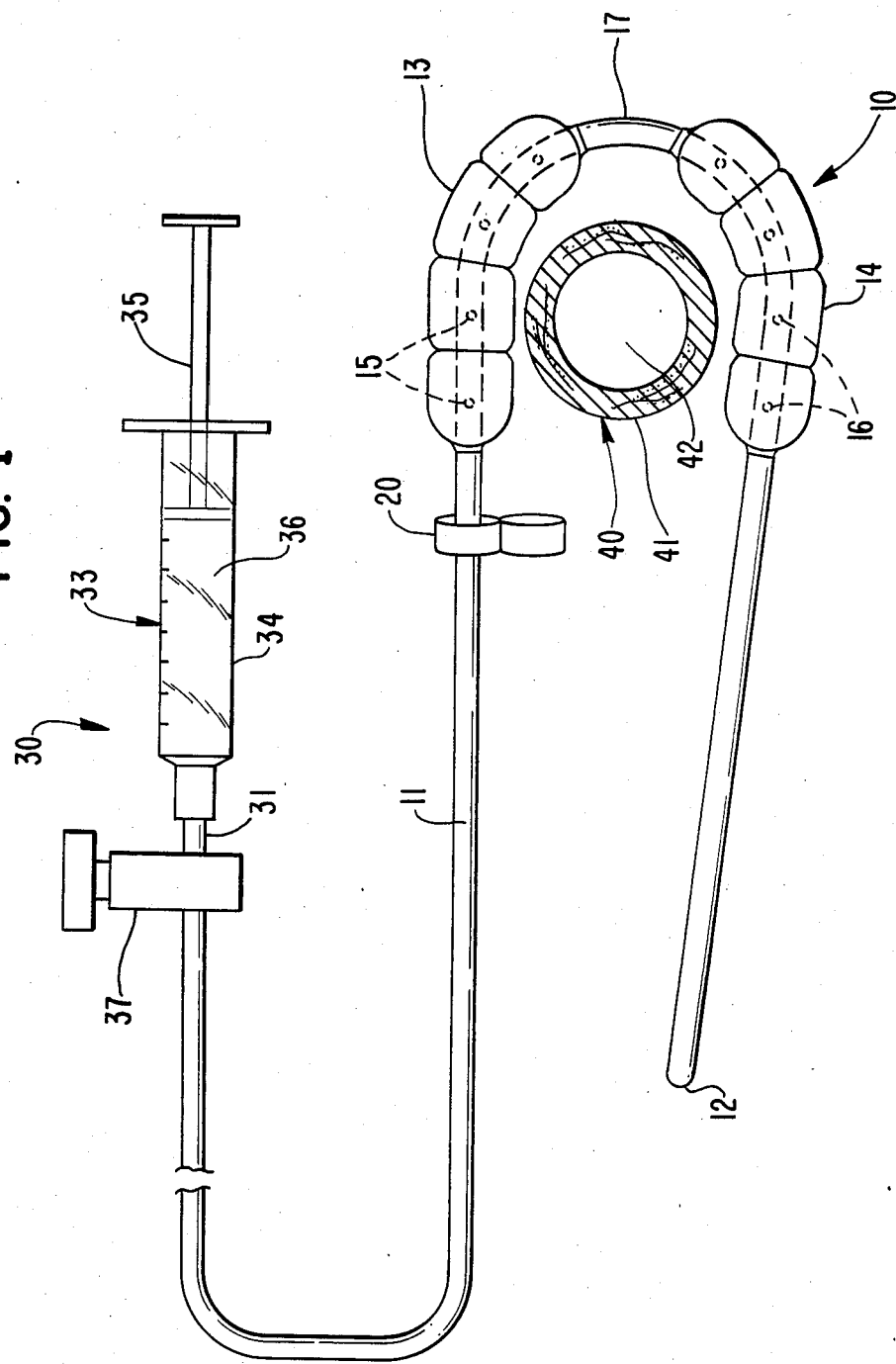
FIG. 1 is a side elevational view, shown partly in section, of a vascular balloon clamp according to one embodiment of the present invention, shown in an open condition before being secured in a closed loop around a vessel, together with one embodiment of a fluid injecting means.

Although specific embodiments of the present invention have been selected for illustration in the drawings, and although specific terminology will be resorted to in describing those embodiments in the specification which follows, it will be understood by those skilled in the art that these descriptions are merely examples of certain embodiments of the present invention, whose scope is defined in the appended claims.

DETAILED DESCRIPTION

Referring now to the drawings, wherein like reference numerals depict like features in the several figures, and especially referring to FIG. 1, there is shown a vascular balloon clamp 10 comprising a hollow flexible catheter 11 having a closed end 12, and a pair of balloons 13, 14. Alternatively, the catheter 11 having a normally open end 12 may be provided with a releasable compression clamp 21 which acts to close off end 12. Clamp 21 may be of any suitable type, such as a spring-loaded clamp with fasteners.

Balloons 13, 14 are roughly cylindrical in shape and form sleeves completely surrounding portions of catheter 11 provided with sets of openings 15, 16, respectively. The ends of both balloons 13, 14 are sealed around the circumference of catheter 11 in any number of ways, such as by adhesive, by a metal clip, by a band of latex or with a suitable plastic binding material such as wrapping with a fine plastic thread.

The term "catheter" as used herein refers to any thin, flexible hollow tube adapted to carry a fluid and suitable for surgical procedures. The catheter 11 may be composed of any number of flexible materials, but preferably comprises a medium density polyethylene or polyurethane suitable for antiseptic introduction into the body. The balloons 13, 14 are preferably composed of an expandable latex or silicone rubber material, also suitable for antiseptic introduction into the body.

Balloon 14 is positioned a sufficient distance from the end 12 of catheter 11 to provide a length of catheter 11 suitable for insertion into a securing means, such as double port keeper 20 and/or clamp 21. Balloons 13, 14 are spaced apart from one another by a predetermined distance 17 along the length of the catheter 11. The size of the balloons 13, 14 as well as their spacing 17 will vary depending upon the size of the vessel 40 being occluded. For instance, most blood conveying vessels, such as arteries, have outer diameters in the range of about 4-40 mm and wall thicknesses, which generally are proportional to the lumen of the vessel, in the range of 1-6 mm. Accordingly, the distance 17 typically will be about 2 mm for the smallest arteries having diameters of about 4 mm. As the vessel size increases, the lengths of the balloons and their spacing 17 necessarily will increase, the combined effect of the two being to maintain substantial parallelism of the occluding surfaces and provide lateral expansion spaces for the vessel wall, as explained more fully below. For the largest vessel on the order of 40 mm in outside diameter the spacing 17 should be on the order of 10-12 mm. For healthy vessels the length of each balloon typically should be on the order of the outer vessel diameter, while the spacing 17, which is related to the thickness of the compressed vessel, should be on the order of twice the vessel wall thickness. If an arteriosclerotic condition is anticipated, a clamp with a larger space 17 can effectively be used to accommodate the pathologically thickened vessel wall.

Figure 2:
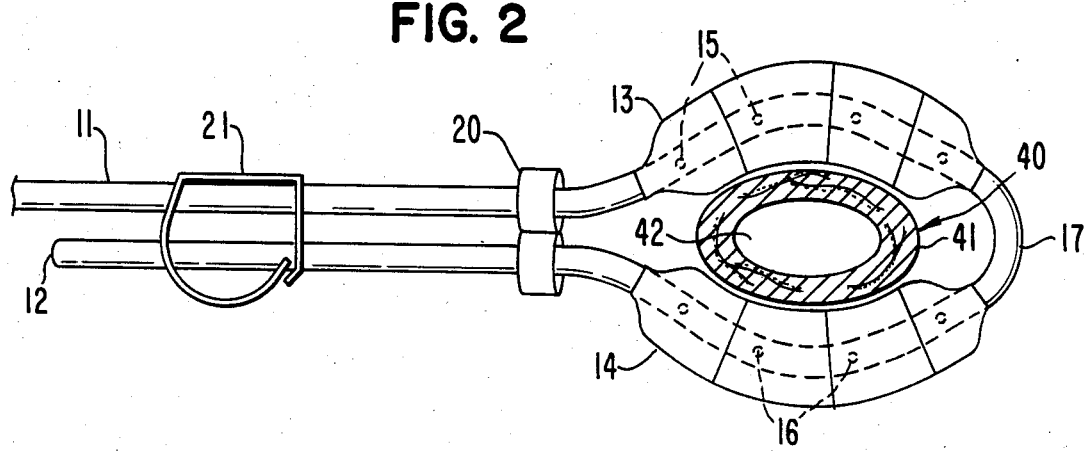
FIG. 2 is a side elevational view, shown partly in section, of the clamp shown in FIG. 1 in a closed or secured condition around the vessel.

Referring now to FIG. 2, there is shown a clamp 10 in a secured condition around vessel 40. The end 12 of catheter 11 has been threaded through the double port keeper 20. In addition, clamp 21 has been positioned in order to secure end 12 against catheter 11 (and in the case of an open end 12, to close off the end of catheter 11). As is clearly shown in FIG. 2, the balloons 13, 14, still in a deflated condition, are presented on substantially opposite sides of vessel wall 41.

As is shown in FIG. 1, the other end of catheter 11 is connected to a suitable fluid source, such as fluid injecting means 30. The illustrated fluid injecting means 30 comprises a syringe 33 having a cylinder 34 and a plunger 35. The syringe 33 contains a fluid 36, which may be either a liquid or a gas. Syringe 33 is connected to the end of catheter 11 so that when the plunger 35 is depressed, the fluid 36 is forced into the hollow catheter 11, through the openings 15, 16 and eventually into balloons 13, 14. A valve 37 on tube 31 may optionally be provided in order to prevent back flow of fluid 36 which would cause the balloons 13, 14 to deflate.

Figure 3:
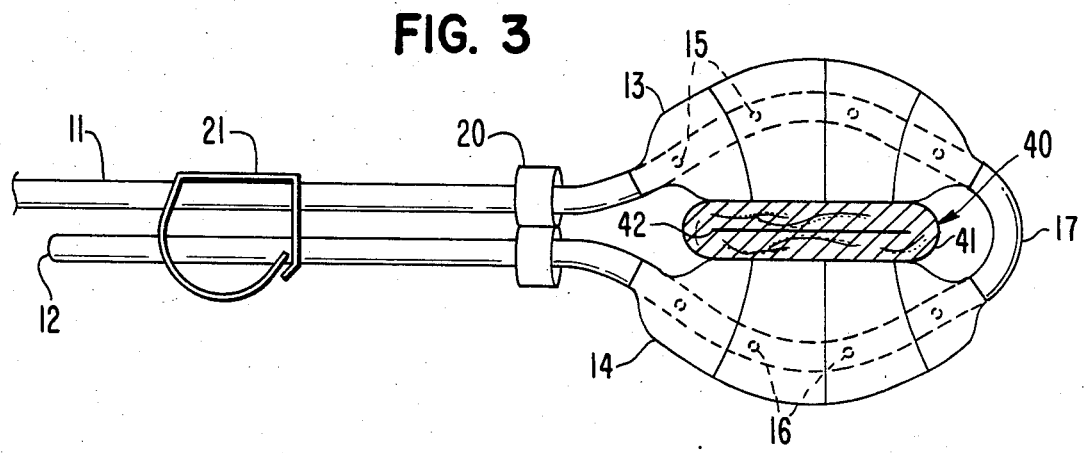
FIG. 3 is a side elevational view, shown partly in section, of the clamp shown in FIG. 2 in an inflated condition.

As is clearly shown in FIG. 3, as the balloons 13, 14 are inflated, they act upon the vessel wall 41 to effectively occlude the lumen 42. As is also clearly shown in FIG. 3, the inflated balloons 13, 14 present substantially parallel opposed occluding surfaces acting upon vessel wall 41 from substantially diametrically opposed points along the circumference of wall 41. Thus, the occluding force delivered by balloons 13, 14 to vessel 40 features substantially straight line parallel compression of vessel 40 by resilient occluding surfaces, whereby vessel 40 is compressed evenly by the two parallel opposed balloon surfaces. The free lateral expansion spaces at the ends of the balloons 13, 14, afforded by the spacing 17 between the balloons and the space between the parallel legs of catheter 11 adjacent keeper 20, allows the vessel to freely expand laterally when compressed without being crushed. It is the combined effect of parallel compression and free lateral expansion space which allows the clamp 10 of the present invention to effectively occlude the inner lumen 42 without imparting significant trauma to vessel 40. It is important in order to achieve these benefits that a sufficient distance 17 be provided between balloons 13, 14 in order to avoid any substantial "tangential" force component which might tend traumatize the vessel.

Figure 4:
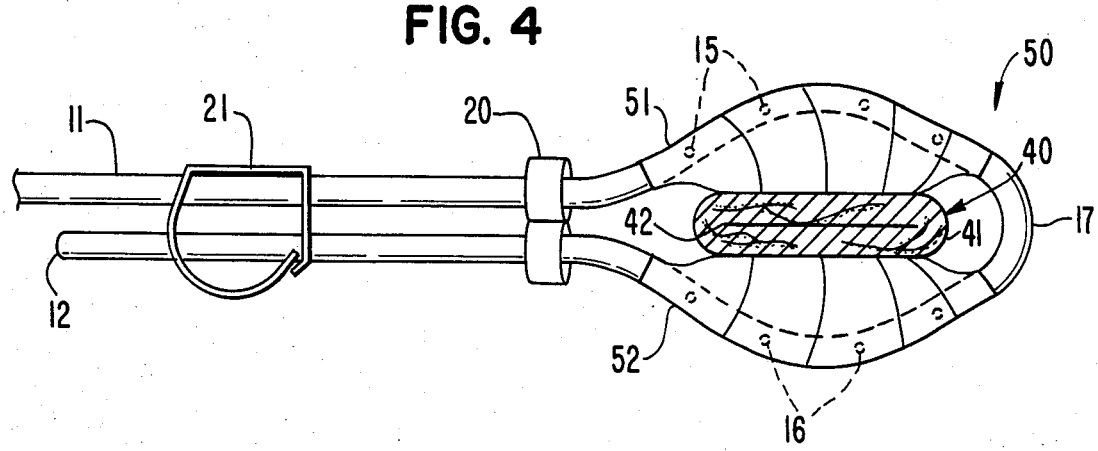
FIG. 4 is a side elevational view, shown partly in section, of another embodiment of a vascular balloon clamp according to the invention also shown in an inflated, secured condition.

Referring now to FIG. 4, there is shown another embodiment of a vascular balloon clamp 50. Clamp 50 also comprises a flexible hollow catheter 11 having a closed (or closable) end 12, a double port keeper 20 and a clamp 21. Clamp 50 further comprises a pair of inflatable balloons 51, 52 positioned around those portions of catheter 11 containing openings 15, 16, respectively. Balloons 51, 52, in addition to being sealed to catheter 11 at their ends, are attached to catheter 11 along their outwardly facing sides. Thus, when the balloons 51, 52 are inflated as shown in FIG. 4, only the inner portions of balloons 51, 52 will expand in order to present parallel opposed occluding surfaces pressing against vessel wall 41.

As is shown most clearly in FIG. 1, the clamping surfaces of balloons 14, 15 are preferably ridged or undulating in order to present surfaces which more effectively grip and compress vessel wall 41.

Although specific embodiments have been described in the specification hereinabove, it will be appreciated by those skilled in the art that a wide variety of equivalents may be substituted for those specific elements and steps of operations described above, without departing from the spirit and scope of the invention as defined in the appended claims.

I claim:

1. A temporary, non-implantable, disposable clamp for temporarily occluding the lumen of a blood vessel during surgery, comprising:
   (a) a flexible hollow catheter adapted to be connected to a fluid source;
   (b) a pair of spaced inflatable balloons, each of the balloons being positioned along and sealed to the exterior of a portion of the catheter and having a length on the order of the vessel diameter, the balloons being in fluid communication with the interior of the catheter and separated by a predetermined distance along the catheter on the order of twice the vessel wall thickness; and
   (c) means for securing the catheter in a closed loop around the vessel, with the balloons presenting substantially parallel, opposed and spaced occluding surfaces on substantially opposite sides of the vessel with lateral expansion spaces for the vessel tissue adjacent the ends of the balloons, whereby inflation of the balloons clamps the vessel therebetween to close the lumen, the vessel wall expanding laterally into the expansion spaces as it is compressed.

2. The clamp as defined in claim 1, wherein the balloons communicate with the interior of the catheter through a plurality of openings in the catheter wall.

3. The clamp as defined in claim 1 wherein the catheter has two leg portions which are adjacent the respective balloons and remote from the predetermined space between the balloons, said two leg portions being substantially parallel and lying alongside one another when the catheter is secured around the vessel.

4. The clamp as defined in claim 3 wherein the securing means is releasable.

5. The clamp as defined in claim 4 wherein the securing means comprises a double port keeper.

6. The clamp as defined in claim 1 wherein the balloons form sleeves around the catheter, the sleeves having ends which are secured in an air-tight manner around the catheter.

7. The clamp as defined in claim 1 wherein the vessel is an artery having a diameter in the range of about 4–40 mm.

8. A method of temporarily occluding a blood vessel during surgery, comprising the steps of:
   (a) securing a hollow flexible catheter in a closed loop around the vessel, the catheter having a pair of inflatable balloons, each of the balloons being positioned along and sealed to the exterior of a portion of the catheter and having a length on the order of the vessel diameter, the balloons being in fluid communication with the interior of the catheter and separated by a predetermined distance along the catheter on the order of twice the vessel wall thickness; and
   (b) injecting a fluid into the catheter to inflate the balloons, the balloons when inflated presenting substantially parallel opposed and spaced occluding surfaces on substantially opposite sides of the vessel with lateral expansion spaces for the vessel tissue adjacent the ends of the balloons, whereby inflation of the balloons clamps the vessel therebetween to close the lumen, the vessel expanding laterally into the expansion spaces as it is compressed.

9. The method as defined in claim 8 wherein the vessel is an artery having a diameter of about 4–40 mm.

10. The method as defined in claim 8 wherein the fluid comprises air.

11. The method as defined in claim 8 wherein the fluid comprises water.

12. The method as defined in claim 8 wherein the step of securing the catheter around the vessel comprises securing two leg portions of the catheter alongside and substantially parallel to one another, said leg portions being adjacent the respective balloons and remote from the predetermined space between the balloons.

13. The method as defined in claim 12 wherein said leg portions are releasably secured together.

* * * * *